United States Patent [19]

Daeschel et al.

[11] Patent Number: 5,451,369
[45] Date of Patent: Sep. 19, 1995

[54] BACTERIOCIDAL SURFACES AND ARTICLES WITH ATTACHED BACTERIOCIN

[75] Inventors: Mark A. Daeschel, Philomath; Joseph McGuire, Corvallis, both of Oreg.

[73] Assignee: The State of Oregon Acting By and Through The State Board of Higher Education on Behalf of Oregon State University, Eugene, Oreg.

[21] Appl. No.: 139,331

[22] Filed: Oct. 18, 1993

Related U.S. Application Data

[63] Continuation of Ser. No. 882,435, May 13, 1992, abandoned.

[51] Int. Cl.6 .............................................. A61L 2/00
[52] U.S. Cl. .................................... 422/28; 422/32; 422/40; 426/323; 426/326
[58] Field of Search ............................ 422/28, 32, 40; 426/106, 323, 326, 334, 335, 532, 133; 514/21

[56] References Cited

U.S. PATENT DOCUMENTS

| | | | |
|---|---|---|---|
| 2,480,010 | 8/1949 | Flett . | |
| 2,858,225 | 10/1958 | Gooding et al. . | |
| 3,390,001 | 6/1968 | Beck . | |
| 3,819,329 | 6/1974 | Kaestner et al. | 426/335 X |
| 3,852,486 | 12/1974 | Walker et al. | 426/335 X |
| 4,740,593 | 4/1988 | Gonzalez et al. | 426/61 |
| 4,851,223 | 7/1989 | Sampson | 424/711 |
| 5,043,176 | 8/1991 | Bycroft et al. | 426/335 |
| 5,059,431 | 10/1991 | Daeschel et al. | 423/13 |
| 5,104,649 | 4/1992 | Jansson et al. | 424/78.31 |
| 5,171,591 | 12/1992 | Whiting | 426/43 |
| 5,186,962 | 2/1993 | Hutkins et al. | 426/61 |
| 5,234,719 | 8/1993 | Richter et al. | 427/384 |
| 5,288,532 | 2/1994 | Juhl et al. | 428/35.2 |

OTHER PUBLICATIONS

McGuire, "On Evaluation of the Polar Contribution to Contact Material Surface Energy," *J. Food Eng.* 12:239–247 (1990).

Arnebrant et al., "Bilayer Formation at Adsorption of Proteins from Aqueous Solutions on Metal Surfaces," *Progr. Colloid & Polymer Sci.* 70:62–66 (1965).

*Primary Examiner*—Robert J. Warden
*Assistant Examiner*—Krisanne M. Thornton
*Attorney, Agent, or Firm*—Klarquist Sparkman Campbell Leigh & Whinston

[57] ABSTRACT

Articles and surfaces are disclosed having antimicrobial activity. Also disclosed are methods for treating surfaces and articles to confer antimicrobial activity. Such articles and surfaces are particularly adapted for food contact use, such as food preparation or packaging. Antimicrobial activity is conferred by applying molecules of a polypeptide bacteriocin, e.g., nisin, such as by contacting the surface or article with a liquid solution of a bacteriocin or bacteriocin mixture. The bacteriocin molecules are attached to the surface or article via any means enabling the molecules to subsequently detach and lethally interact with susceptible bacteria deposited on the treated surface or article. Such detached bacteriocin molecules can also kill susceptible bacteria present on foods or other substances that contact the surface or article. Attached bacteriocins are stable to drying, water rinsing, and freezing, even for long periods.

9 Claims, 3 Drawing Sheets

BACTERIOCIDAL SURFACES AND ARTICLES WITH ATTACHED BACTERIOCIN

This application is a continuation, of application Ser. No. 07/882,435, filed on May 13, 1992, now abandoned.

FIELD OF THE INVENTION

The present invention pertains to coating or otherwise treating surfaces and articles with an antimicrobial substance.

BACKGROUND OF THE INVENTION

The ability of pathogenic and food-spoilage microorganisms to adhere to surfaces is widely recognized as a serious problem. Current evidence suggests that microorganisms attached to surfaces are less susceptible to the killing effects of sanitizers, disinfectants, and sterilants. In the food industry, bacteria residing on food-contact surfaces of food processing machinery, food preparation implements, and packaging can be a difficult-to-eradicate source of dangerous infection. In many instances, increasing the concentration of chemical sterilants is impracticable. High sterilant concentrations can also pose a health risk to personnel using these agents. High concentrations of some sterilants can cause damage to the surfaces or articles exposed thereto. Also, such high levels can result in unacceptable levels of chemical residuals in the surfaces which can pass to other materials, such as food, that subsequently contact the surfaces. Finally, higher chemical concentrations do not necessarily result in greater sanitation efficiency.

In view of the foregoing, there is a need for a way to inhibit the attachment of bacteria to substantially solid surfaces and articles, particularly to such surfaces and articles intended for food contact use.

There is also a need for a way to prevent bacterial colonization of substantially solid surfaces and articles, particularly such surfaces and articles intended for food-contact use.

There is also a need for food-contact surfaces and articles exhibiting antimicrobial activity.

There is also a need for such surfaces and articles capable of killing bacteria present in substances such as food brought into contact with such surfaces and articles.

There is also a need for food-contact surfaces and articles having an antimicrobial characteristic that does not add ingestive toxicity or altered flavor or odor to foods contacting such surfaces and articles.

There is also a need for a way to render food-packaging materials capable of killing bacteria in foods that contact the materials.

There is also a need for a method for preparing a surface or article for food-contact use so as to substantially prevent transfer of bacteria from the surface or article to food ultimately contacting the surface or article.

In addition, there is a need for such an agent that is non-toxic and ingestible.

SUMMARY OF THE INVENTION

The foregoing needs are filled by one aspect of the present invention which provides articles and surfaces exhibiting antimicrobial activity that imparts no ingestive toxicity or altered flavor to substances such as foods contacting such articles and surfaces. According to another aspect of the present invention, methods are provided for conferring a bacteriocidal character to substantially solid surfaces and articles, particularly such surfaces and articles adapted for food-contact use.

As used herein a "substantially solid" surface is a surface that is not a liquid surface. Substantially solid surfaces include surfaces of glassy and rubbery materials as well as surfaces of materials conventionally regarded as "solid" to the touch such as metal, plastic, ceramic, and wooden surfaces.

In particular, a substantially solid surface, such as a food-preparation surface, a food-processing surface, a food-packaging surface, or the surface of an article such as a food preparation implement, is treated with a solution comprising one or more types of bacteriocins.

Bacteriocins are polypeptide compounds, produced by various bacteria, that have antimicrobial properties. Although a number of different bacteriocins are known, the most-studied and currently most widely used bacteriocin is nisin, which has been approved in a number of countries as a food additive capable of inhibiting bacterial growth in various foods without altering flavor or odor. Bacteriocins produced by lactic-acid bacteria (and probably other bacteriocins, although this has not yet been proven) are ingestively non-toxic; i.e., they can be ingested by higher animals, including humans, without apparent ill effects, even in large doses. Apparently, they are digestively degraded just like any other ingested proteinaceous material to their constituent amino acids.

According to another aspect of the present invention, a substantially solid surface can be rendered bacteriocidal merely by contacting the surface with an aqueous solution of a bacteriocin or a mixture of bacteriocins. As a result of their amphipathic nature, bacteriocin molecules become attached to the surface by adsorption, an example of non-covalent attachment. Once adsorbed to the surface, the bacteriocin molecules are surprisingly resistant to removal therefrom by rinsing with water. The bacteriocin molecules also retain their antimicrobial activity after drying, allowing bacteriocin-treated surfaces to be stored and used at times and places remote from the time and place of bacteriocin treatment.

Bacteriocin molecules must become detached from a bacteriocin-treated surface in order to function optimally as bacteriocidal agents. Thus, contact of a bacteriocin-treated surface with a food material, particularly a material having a significant liquid content, will enable bacteriocin molecules to detach from the surface so as to enable the molecules to lethally interact with susceptible bacteria present in the food material and located near the contact surface. Bacteriocin-treated surfaces can also kill susceptible bacteria that become deposited directly on the treated surfaces.

Bacteriocin-treated surfaces can also be used in food packaging or other use wherein food is in contact with surfaces for extended periods of time.

Bacteriocin molecules can also be attached to a surface by direct covalent means or by microencapsulating the molecules and attaching the microcapsules to the surface. Both these methods are generally known in the art, as used for application other than attaching antibacterial substances to surfaces.

Surfaces of a wide variety of materials can be treated with bacteriocins according to the present invention, including hydrophilic and hydrophobic surfaces. Such materials include virtually all materials generally recognized as safe for food-contact use, including for food-packaging use.

BRIEF DESCRIPTION OF THE DRAWINGS

The invention will now be further described, particularly by way of examples, with reference to the following drawings, in which.

DETAILED DESCRIPTION

Figure 1:
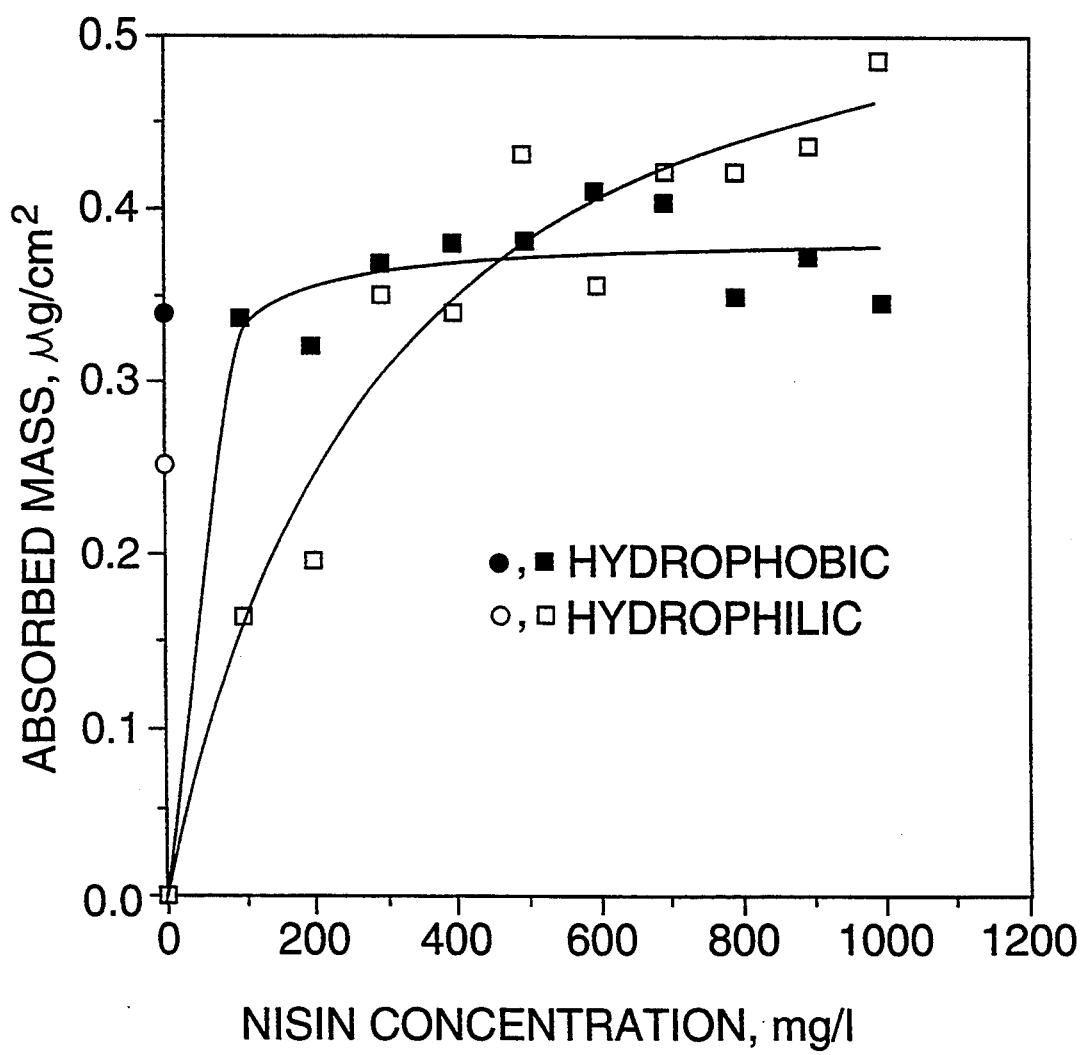
FIG. 1 is a plot of nisin adsorption isotherms for representative hydrophobic surfaces (closed squares) and hydrophilic surfaces (open squares). The masses of nisin remaining on each type of surface after 12-hours, post-absorption exposure to buffer solution are indicated by the closed circle (hydrophobic surface) and open circle (hydrophilic surface).

We discovered that various solid surfaces and articles, including hydrophobic and hydrophilic surfaces as found in food-processing equipment, food preparation implements, and food packaging, can be treated with a composition comprising antimicrobial proteins termed bacteriocins, wherein molecules of the bacteriocin subsequently remain attached to the surface for sustained bacteriocidal action.

Bacteriocins are normally produced by a number of gram-positive bacteria. The various bacteriocins differ greatly in their bacteriocidal properties. However, they have the following general characteristics: Bacteriocins are generally hydrophobic polypeptides. Molecular weight can vary considerably, depending upon the particular bacteriocin. Some bacteriocins include unusual amino acids in their polypeptide structure. The bacterial action of bacteriocins is very rapid. Bacteriocins tend to bind to specific receptor(s) on bacterial cell walls, ultimately destabilizing normal functions of the bacterial cell membrane. The range of bacteriocin-susceptible species varies widely depending upon the particular bacteriocin; in general, specific strains of gram-positive bacteria are sensitive. However, the same strains are not sensitive to all bacteriocins. Bacteriocins are generally very stable; they retain their bacteriocidal properties even after exposure to high heat. They retain antimicrobial activity over a wide pH range, but are generally more active in acid pH. Most are stable to freezing and drying, even for extended periods. Their activity is usually lost upon exposure to proteolytic enzymes such as gastric proteinases. Of those bacteriocins tested to date, none have been found to be toxic to animals.

Bacteriocins have been isolated from a large number of bacterial strains, including strains from the following species: *Streptococcus lactis*, *Streptococcus salivarius*, Leuconostoc species, *Pediococcus acidilactici*, *Pediococcus pentosaceus*, *Lactobacillus acidophilus*, *Lactobacillus plantarum*, *Lactobacillus delbrueckii*, *Lactobacillus helveticus*, *Lactobacillus casei*, *Lactobacillus brevis*, *Lactobacillus fermentum*, *Lactobacillus sake*, *Lactobacillus gasseri*, *Lactobacillus viridescens*, *Carnobacteria piscicola*, *Bifidobacterium spp.*, *Enterococcus faecium*, and *Propionibacterium thoenii*.

Several bacteriocins have been demonstrated to have a wide antimicrobial spectrum, including the bacteriocins nisin, pediocin AcH, and pediocin PA1, all produced by lactic-acid bacteria. Another wide-spectrum bacteriocin is propionicin PLG 1. The other known bacteriocins have relatively narrower activity spectra.

Most of the known bacteriocins have not been studied in detail. The wide-spectrum bacteriocins have been studied more, probably because of their potential, as well as actual, utility.

Pediocin AcH, first identified in 1984, is efficacious in controlling a wide range of spoilage and pathogenic gram-positive bacteria in liquid milk, ice cream, cottage cheese, fresh and cooked beef, and ground beef. Purified pediocin AcH has a molecular weight of 2700 daltons.

Pediocin PA1 has been found to control gram-positive bacterial populations in cottage cheese, cheese spreads, and milk. Pediocin PA1 when purified has a molecular weight of 16,500 daltons.

Nisin has been studied the most extensively of all known bacteriocins. Nisin has been recognized for over fifty years for its antimicrobial activity and has been studied in many different food systems including dairy products, meats, fish, vegetables, wine, and beer. Nisin is effective in preserving these foods against many gram-positive spoilage and pathogenic bacteria without altering the flavor of these foods. Nisin has also been approved in many countries, including the United States, for use in specific foods. (In particular, nisin has recently been approved by the United States Food and Drug Administration for use in pasteurized cheese spreads.) Against nisin-sensitive spore-formers, nisin is inhibitory to both vegetative cells and spores.

Nisin is naturally produced by *Lactococcus lactis* bacteria. When purified, nisin has a molecular weight of 3510 daltons and contains 34 amino acids (including four unusual amino acids).

Purified dry nisin powder retains its potency indefinitely under refrigeration storage. However, its activity appears to gradually decline in food systems at refrigeration temperature, as has been observed in cheese, canned mushrooms, chocolate milk, cooked ham, and other food products.

Treatment of nisin with α-chymotrypsin, pancreatin, and ficin can destroy the antimicrobial activity of nisin. However, trypsin, pepsin, erepsin, diastase, and carboxypeptidase A do not appear to inactivate nisin. Thus, nisin is stable against a number of proteolytic and other enzymes normally found in foods of animal, plant, and microbial origins, particularly against heat-stable proteases.

Nisin is particularly stable under acidic pH and is less stable when exposed to pH environments greater than about 8. At pH 11, nisin activity can be lost rapidly. Fortunately, many foods have either a substantially neutral or somewhat acidic pH.

Nisin is particularly heat-stable under acidic conditions and can survive autoclaving temperatures in acidic solution. The heat-stability of nisin decreases as the pH is increased.

The toxicity of the bacteriocins appears to be very low. For example, nisin is substantially non-toxic to laboratory animals, wherein the $LD_{50}$ of nisin is similar to sodium chloride. The Safety of Nisin as a Food Additive, Technical Information Sheet No. 2/88, Aplin and Barrett, Ltd., England (1988); "Specification for the Identity and Purity of Food Additives and Their Toxicological Evaluation: Some Antibiotics," 12th Report of the Joint FAO/WHO Expert Committee on Food Additives, WHO Technical Report, Series #430, World Health Organization, Geneva, Switzerland. The low toxicity probably reflects the substantially complete digestibility of these compounds.

According to the present invention, solid surfaces and articles intended for food contact are treated with a solution of a bacteriocin or mixture of bacteriocins. During such "treatment," bacteriocin molecules become adsorbed onto the surfaces. Thus, the surfaces become "armed" with an arsenal of bacteriocidal proteins that kill sensitive bacteria that subsequently contact the surfaces.

In general, proteins are very surface-active; their strongly amphipathic nature (i.e., having both hydrophilic and hydrophobic groups) give them great stability in the adsorbed state. These properties are also shared by the bacteriocins. For example, nisin, a representative bacteriocin-type polypeptide, can become adsorbed to a large variety of surfaces, including both hydrophilic and hydrophobic surfaces. Also, bacteriocins such as nisin appear to be quite stable when adsorbed to a surface, including after drying.

Many types of polypeptides, including bacteriocins can be immobilized on solid surfaces by either covalent or non-covalent attachment. For example, the properties of nisin are such that attachment by multiple, non-covalent bonds is energetically favorable at a variety of interfaces. To non-covalently attach nisin to a solid surface, the surface is preferably first cleaned to remove foreign material adhering thereto and then simply contacted with a nisin solution for a time, such as several minutes, depending on contact surface chemical properties. The surface can then be rinsed with water, although rinsing is not necessary. Nisin molecules remain adsorbed to the surface during rinsing and even after the surface is allowed to dry.

Covalent attachment of bacteriocin molecules to a solid surface may have particular utility whenever, for example, an extremely long "shelf life" of the bacteriocin-treated surface is desired or required. Methods and materials for covalently attaching polypeptides to solid surfaces are well-known among persons such as biochemists who use such methods and materials, for example, for affinity chromatography, preparing antibody conjugates, immobilized enzymes, and other uses. At or before actual time of use, however, it may be necessary to secondarily treat the surface so as to break the covalent bonds linking the bacteriocin molecules to the surface, thereby rendering the molecules capable of detaching from the surface.

Another way of attaching bacteriocin molecules to a surface, which offers a long shelf life without the need for making and breaking covalent bonds, is to encapsulate the molecules in microcapsules or analogous vehicles that are subsequently attached to the surface. Microencapsulation technology is well-known in such arts as carbonless copy paper and "scratch-and-sniff" technology. The microcapsules can be formulated to release their bacteriocin contents when contacted with an aqueous or oily substance, when heated to a certain temperature, or when subjected to some other environmental influence such as abrasion.

Another way to "apply" bacteriocins to a surface is to prepare a biofilm on the surface of the corresponding bacteriocin-producing bacteria. Preferably, the attached bacteria have been selected or genetically altered to produce hyper-normal amounts of the corresponding bacteriocin.

For adsorption, bacteriocins are preferably applied to a surface as a buffered solution. The amount of the bacteriocin that adsorbs to the surface will vary depending upon the particular bacteriocin and the surface. For example, a representative range of nisin concentration after application to a surface is about 0.10 μg to about 1.00 μg per square centimeter of surface. For nisin, the pH of the buffer is preferably within a range of about 2 to about 7. Other bacteriocins may have other optimal pH ranges. Ionic strength of the buffer does not appear to limit the amount of nisin that adsorbs to a surface. Other substances can also be present in the nisin-containing buffer without causing substantial degradation of nisin activity, including alcohol (10 to 15% w/v), NaCl (up to about 10% w/w) and glucose or other sugar (up to about 20% w/w).

Application of bacteriocins to a surface can be by any of various methods currently known in the art, including simple methods such as spraying, dipping, or wiping. No special equipment or sophisticated methods are required.

After a surface or article is treated with a bacteriocin solution as described above, the surface or article can be employed as a food-contact surface.

Nisin has high stability, having an ability to retain bacteriocidal activity for extended periods (e.g., 16–24 months) at ambient temperatures (0°–40° C.). Humidity does not appear to degrade bacteriocidal activity, which is consistent with the fact that nisin is active in aqueous solutions. The more limited data available for other bacteriocins indicates that they have similar stability.

Representative food-contact surfaces suitable for "treatment" with one or more bacteriocins include, but are not limited to: paraffin, viton, polytetrafluoroethylene, thermoplastic and crosslinked polyethylenes, glycol-modified polyethylene terephthalates, ethylene-vinyl alcohol polymers, polypropylenes, polyamides, acetals, stainless steels, copper alloys, aluminum alloys (including anodic coatings thereon), acrylics, polycarbonates, polyesters, wood, glass, ceramics, porcelain, polyvinyl chloride, polyvinylidene chloride, regenerated celluloses, silicones, polysulfones, phenolics, melamine polymers and copolymers, poly(methyl methacrylates), and polystyrene. One or more such materials can be found in a wide variety of food-contact surfaces, including food-processing machinery, food-preparation surfaces and implements, and food packaging.

Our research (see Example 2, hereinbelow) indicates that adsorbed bacteriocin must desorb from a surface in order to exhibit bacteriocidal activity. For example, nisin is a small polypeptide that must traverse through the bacterial cell wall to elicit lysis of the cell membrane of a susceptible bacterium. Therefore, it would appear that nisin molecules that remained attached to a surface would not be able to lethally interact with bacterial cells. When nisin-treated surfaces are contacted with substances such as food, particularly abrasive substances or substances having a significant moisture or other liquid component, the nisin molecules are removed (desorbed) from the surface. The desorbed molecules, then, become available to kill any susceptible bacteria present in the food or other substance contacting the surface. It will be appreciated that surfaces of food-processing machinery, food preparation implements, and the like that are contacted by large amounts of food will eventually experience removal of substantially all the adsorbed bacteriocin. Thus, it will be necessary in such instances to re-treat the surfaces as required so as to replenish the population of bacteriocin molecules thereon. The frequency of such re-treatment will depend on a number of factors including type of surface, type of material (such as food) contacting the surface, amount of liquid(s) in the food, type of liquid in the food, volume of food material contacting the surface per unit time, pressure and temperature conditions of food contact, hydrophilicity or hydrophobicity of the food material, surfactant properties of the food material, and other factors. However, it is within the purview of persons skilled in the art to readily ascertain, such as by routine bacteriological assays of residual bacterial flora present on a food-contact surface, when the surface is no longer exhibiting antimicrobial action.

In order to further illustrate the invention, the following examples are given.

EXAMPLE 1

This example is an investigation of the binding ability of nisin on hydrophilic surfaces and on such surfaces made strongly hydrophobic by silanization. As representative hydrophilic surfaces, we selected monocrystalline silicon because this material is homogeneous, has substantially no pores or surface cavities, and has optical properties amenable to analysis using a laser beam.

Optically flat, monocrystalline silicon wafers (Wacker Siltronic Corp., Portland, Oreg.) having 1-0-0 orientation and a resistivity of 0.1 to 0.16 ohm.cm were cut into 1×2 cm wafers using a tungsten knife. The wafer surfaces were polished to a mirror finish.

A first quantity of wafers was made hydrophilic by oxidation wherein the wafers were immersed in a mixture of $NH_4OH:H_2O_2:H_2O$ (1:1:5) at 80° C. for 15 minutes. The wafers were then rinsed using distilled deionized water followed by an immersion in $HCl:H_2O_2:H_2O$ (1:1:5) for 15 minutes at 80° C. Each wafer was then rinsed using distilled deionized water and stored in 20 mL of 50% ethanol/water solution until use.

A second quantity of wafers was made hydrophobic by silanization with dichlorodimethylsilane according to Jonsson et al., *J. Colloid Interface Sci.* 90:148-163 (1982).

Hydrophilicity and hydrophobicity were confirmed by contact angle analysis according to McGuire, *J. Food Eng.* 12:239-247 (1990), incorporated herein by reference. In brief, hydrophobicity was determined by measuring the nondispersive component of the work $W_a^p$ required to remove water from a surface, wherein $W_a^p$ is defined according to equation (1) in said McGuire reference. This value was gained using contact-angle methods, and all food-contact surfaces can be analyzed in this way. (Water formed a contact angle of less than 10 degrees on hydrophilic silicon and a contact angle of greater than 100 degrees on hydrophobic surfaces.) Although the value of $W_a^p$ (and, therefore, $W_a$ $_{water}^p$, id.) depends upon selected liquid and solid properties experience suggests that $W_{a\ water}^p$ ranges between zero to about 100 mJ/m². A low value indicates strong hydrophobicity and a high value indicates strong hydrophilicity.

For evaluation of nisin adsorption thereto, hydrophilic silicon wafers were removed from the 50% ethanol solution in which they were stored, rinsed in distilled deionized water, and dried with nitrogen. Hydrophobic wafers were rinsed using trichloroethylene immediately after silanization, rinsed in acetone, rinsed in ethanol, and dried with nitrogen. The optical constants of the wafers were determined by ellipsometry prior to exposing the wafers to a nisin solution.

A high-potency grade of nisin was obtained from Aplin and Barrett Ltd., Dorset, UK. Nisin activity was nominally $45.5 \times 10^6$ Units/g. Nisin was added to 0.01M monobasic sodium monophosphate (pH 4.5) to ensure complete solubilization of the nisin. Dibasic sodium monophosphate (0.01M) was added to solubilized nisin to raise the pH to 6.0. Thus a final "stock" nisin concentration of 1 mg/mL was obtained. Solutions having various concentrations of nisin were prepared by diluting the stock nisin solution with 0.01M sodium phosphate buffer (pH 6.0). The silicon wafers were individually contacted with a 15 mL volume of a different nisin solution for 8 hours. Afterward the wafers were rinsed three times with distilled deionized water to remove any nisin not bound tightly to the wafer surfaces. The wafers were then dried in nitrogen, stored in a desiccator for about 12 hours, then removed for ellipsometric analysis. Triplicate samples were simultaneously prepared and tested for each nisin solution.

As mentioned above, thickness and refractive index studies of the nisin-coated wafers were performed by ellipsometry. Ellipsometry is a way to analyze changes in the state of polarized light resulting from reflection of the light from a film-covered surface such as a surface coated with a protein film. The state of polarization is defined by phase and amplitude relationships between the p-wave (wave in the plane of incidence) and the s-wave (wave normal to the plane of incidence) components of electromagnetic radiation. In general, reflection of polarized light from a surface causes a change in the relative phases of p and s waves and a change in the ratio of their amplitudes. Reflected light is characterized by the angle $\Delta$, defined by the change in phase, and the angle $\psi$, the arctangent of the factor by which the amplitude ratio changes. Resolution of measured $\psi$ and $\Delta$ angles for each nisin-covered wafer surface into values of nisin-film thickness and refractive index was performed using a computer program written in our laboratory based on calculations described by McCracken et al., *J. Res. NBS A. Physics and Chemistry* 67A:363-377 (1963).

Once values for film thicknesses and refractive indices were obtained, the adsorbed mass of nisin films (immersed in buffer) were calculated by an application of the Lorentz-Lorenz relationship as experimentally verified by Cuypers et al., *J. Biol. Chem.* 258:2426-2431 (1983), wherein the absorbed mass of protein (in mg/cm²) is given by:

$$\Gamma = (0.3) \cdot d \cdot f(n) \\ (n_f - n_b)/[(A_p/M_p) - V_{20}(n_b^2 - 1)/(n_b^2 + 2)] \quad [1]$$

where $f(n) = (n_f + n_b)/[(n_f^2 + 2)(n_b^2 + 2)]$; $\Gamma$ (in μg/cm² is the adsorbed mass of nisin; d (in nm) is the nisin film thickness; $A_p$ (in cm³/mol) is the molar refractivity of nisin; $M_p$ (in g/mol) is the molecular weight of nisin; and $V_{20}$ (in cm³/g) is the partial specific volume of nisin at 20° C. The refractive indices $n_f$ and $n_b$ are of a "mixed" nisin-buffer film and of the pure buffer, respectively.

If protein molecules remain on a surface after rinsing are dried, the dried film can be regarded as a "mixed" film consisting of protein and air. Thus, $n_b = n_{air} = 1.000$, and equation [1] simplifies to $$\Gamma = (0.1) \, d(M_p/A_p)(n_f^2 - 1)/(n_f^2 + 2). \quad [2]$$

For nisin, $M_p/A_p = 3.72$ g/cm³. $A_p$ is calculated by summing individual molar refractivities of the amino acids in nisin, excluding the dehydro residues. Molar refractivity data for the common amino acid resides can be found in Pethig, *Dielectric and Electronic Properties of Biological Materials,* Wiley, N.Y., (1979). The value of $M_p$ then becomes the sum of the molecular weights of the amino acids in nisin (excluding the dehydro residues).

With each wafer, ellipsometric measurements were made at each of about 15 to 20 different surface locations using an automated ellipsometer (model no. L104B, Gaertner Scientific Corp., Chicago Ill.). The light source was a 1-mW helium-neon laser having a beam wavelength of 6328 Å impinging on the surfaces of the wafers at an incident angle of 70°. Using a software program, the optical constants $\psi$ and $\Delta$ for bare silicon surfaces and for adsorbed nisin films were determined.

The relationship between adsorbed mass of nisin $\Gamma$ and its apparent equilibrium concentration may be described by more than one model or equation. One model is the Langmuir-type model having the form $$\Gamma = \Gamma_{max} C_{eq}/(a + C_{eq}) \qquad [3]$$

We used this model to describe nisin adsorption on both hydrophobic and hydrophilic wafer surfaces. In equation [2], $C_{eq}$ is the apparent equilibrium concentration of nisin (in mg/L); $\Gamma_{max}$ is the plateau value of adsorbed mass of nisin; and "a" (in mg/L) is a constant wherein $\Gamma_{max}/a$ is the initial slope of a plot of $\Gamma$ versus $C_{eq}$. Assumptions underlying the Langmuir adsorption isotherm include a monolayer film, a homogeneous surface, and no lateral interaction among adsorbed protein molecules. Although equation [3] resembles a Langmuir isotherm, it should not be taken to imply or assume any of its fundamental premises.

The effect of silicon surface silanization on nisin adsorption isotherms is illustrated in FIG. 1. That is, FIG. 1 shows isotherms associated with nisin absorption to a hydrophobic surface and to a hydrophilic surface. As can be seen, nisin adsorption to the hydrophobic surface exhibited a steep initial slope followed by immediate attainment of an adsorption plateau. Nisin adsorption to the hydrophilic surface exhibited a lower surface affinity at low concentrations. However, the affinity of nisin for the hydrophilic surface steadily increased with nisin concentration and did not attain a plateau value in the concentration range 0.1 to 1.0 mg/mL.

Proteins can exist in multiple conformational states and most proteins are believed to change conformation during adsorption. Protein molecules are also believed to, in general, change conformation to a greater extent on a hydrophobic surface compared to a hydrophilic surface. This difference is believed to be due to relatively strong hydrophobic interactions between the solid surface and hydrophobic regions of the protein molecules which cause distortion of the protein molecules such that the molecules become more extended ("flattened"). Thus, each protein molecule covers a larger area of the hydrophobic surface than would otherwise be predicted from the native conformation of the molecules. The repulsive force normally existing between protein molecules in their native conformation is probably decreased for such adsorbed molecules. With proteins adsorbed to a hydrophilic surface, in contrast, forces acting between the surface and the protein molecules are generally lower in magnitude. Thus, any conformational changes experienced by the protein molecules are likely smaller, thereby preserving greater repulsive forces between adsorbed protein molecules. Hence, one would normally expect fewer protein molecules to adsorb to a hydrophilic surface than to a hydrophobic surface.

We surprisingly found, however, that nisin behaved differently on hydrophobic and hydrophilic surfaces than most proteins, according to the above, would be expected to behave. In fact, as shown in FIG. 1, greater amounts of nisin adsorbed to the hydrophilic wafer rather than the hydrophobic wafer. This anomalous result was probably a result of nisin's unusual chemical properties. Nisin is believed to be a relatively inflexible protein, due to its small number of amino acid and its five thioether crosslinks forming internal polypeptide rings. Nevertheless, nisin is a hydrophobic protein, and its profile of adsorption to the hydrophobic wafer surface was consistent with adsorption being entropically driven. Since the nisin molecules apparently underwent more conformational flattening on the hydrophobic surface, they apparently retained less powerful intermolecular repulsive forces. The upper limit (about 0.36 mg/cm$^2$) is consistent with formation of a nisin monolayer on this hydrophobic surface. On the hydrophilic surface, in contrast, no upper limit was apparent, as shown in FIG. 1, although the adsorption profile shows definite signs of reaching a maximum at higher nisin concentrations. The reason for this is unclear. For some reason, the packing density of nisin molecules on a hydrophilic surface may be greater than on a hydrophobic surface. It is also possible that nisin forms a thicker adsorbed layer on a hydrophilic surface than on a hydrophobic surface.

Adsorption does not appear to reverse when the nisin-coated wafers are placed in more dilute solutions (see FIG. 1, circles). This result implies that multiple non-covalent interactions serve to hold the molecules in place on both hydrophilic and hydrophobic surfaces.

Nisin adsorption to hydrophilic surfaces (such as the surfaces of a hydrophilic silicon) is believed to result from electrostatic interactions between nisin molecules and the surfaces. At pH 6, hydrophilic silicon is negatively charged with an isoelectric point of about 2, and nisin is positively charged. Conceivably, at low nisin concentrations, electrostatic interactions between nisin molecules and a hydrophilic surface could be somewhat reduced due to surface "shielding" by counterions. At greater nisin concentrations, shielding would have a lesser effect.

EXAMPLE 2

This example is an investigation of the antimicrobial activity of nisin adsorbed to silicon wafers treated to exhibit hydrophilic properties.

The activity of adsorbed nisin was evaluated by a bioassay performed as follows: Petri dishes (150×25 mm) containing MRS agar (Difco, Detroit, Mich.) were seeded with 0.1% v/v of a standardized overnight culture of *Pediococcus pentosaceus* strain FBB61-2 bacteria. Silicon wafers having hydrophilic surfaces were prepared as described above. Such wafers were prepared with and without adsorbed nisin. Wafers were placed face down directly onto the seeded agar surfaces. The Petri dishes were then incubated at 4° C. for 24 hours, then incubated at 37° C.

Figure 2:
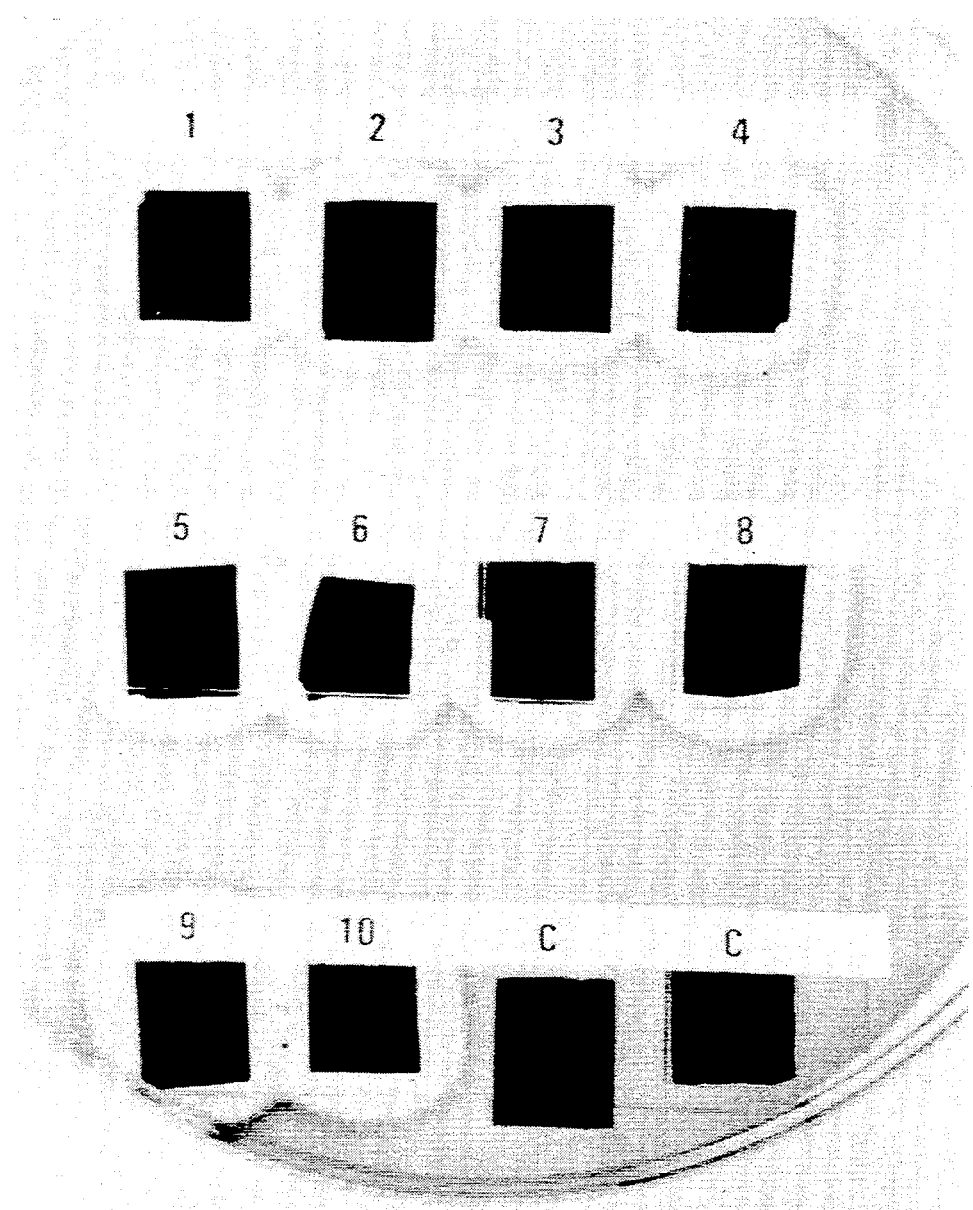
FIG. 2 shows diffusible antimicrobial activity of various concentrations of nisin previously adsorbed on representative hydrophilic surfaces.

Referring to FIG. 2, the silicon wafers numbered 1–10 were subjected to adsorption of nisin from 0.1 to 1.0 mg/mL nisin solutions, respectively (in 0.1 mg/mL increments). The diameter of the inhibition zone around nisin-containing wafers was generally proportional to the $\log_{10}$ concentration of the nisin solution to which the wafers were exposed for nisin adsorption. Qualitatively, it can be seen in FIG. 2 that the amount of nisin antimicrobial activity associated with the nisin-coated wafers (as indicated by the diameters of the respective inhibition zones) corresponds to the mass of nisin that actually adsorbed to the respective wafer as shown in FIG. 1; i.e., the smallest inhibition zone corresponded with the smallest adsorbed mass of nisin. A similar trend was observed with wafers having hydrophobic surfaces to which nisin was adsorbed (data not shown).

Desorption of nisin from the wafer surfaces is believed to be essential in order for the nisin to demonstrate antimicrobial activity. (Nisin is a small polypeptide which must traverse through the microbial cell wall to elicit lysis of the cell membrane.) Thus, while adsorbed to a surface, nisin would probably not be able to exhibit antimicrobial activity.

EXAMPLE 3

This example is an investigation of how well nisin that has adsorbed into a surface withstands "rinsing" without desorbing from the surface.

Nisin was adsorbed to hydrophilic and hydrophobic silicon wafers as described in example 1. We then attempted to desorb nisin from the wafers by placing 50 $\mu$L of 0.01M phosphate buffer (pH 6.0) containing 1% polyoxyethylene sorbitan (Tween 80) on each wafer and "agitating" the droplet over the entire wafer surface using a pipette tip. The 50 $\mu$L droplet was then transferred to 5.6-mm diameter wells that had been made in seeded agar. As controls, we also attempted to desorb nisin from nisin-coated wafers using the phosphate buffer without Tween 80.

Even though adsorbed nisin was resistant to desorption by rinsing with buffer without Tween 80, nisin did desorb when the nisin-coated wafers were placed on the microbial medium in the bioassay petri plates (see Example 2). Tween 80, a commonly used food emulsifier and a component of the MRS agar medium used in this study, has been shown to enhance nisin activity in milk. Tween 80 can also displace proteins from the surfaces of milk fat globules. Phosphate buffer containing Tween 80 was able to desorb nisin from the surfaces of the wafers.

Figure 3:
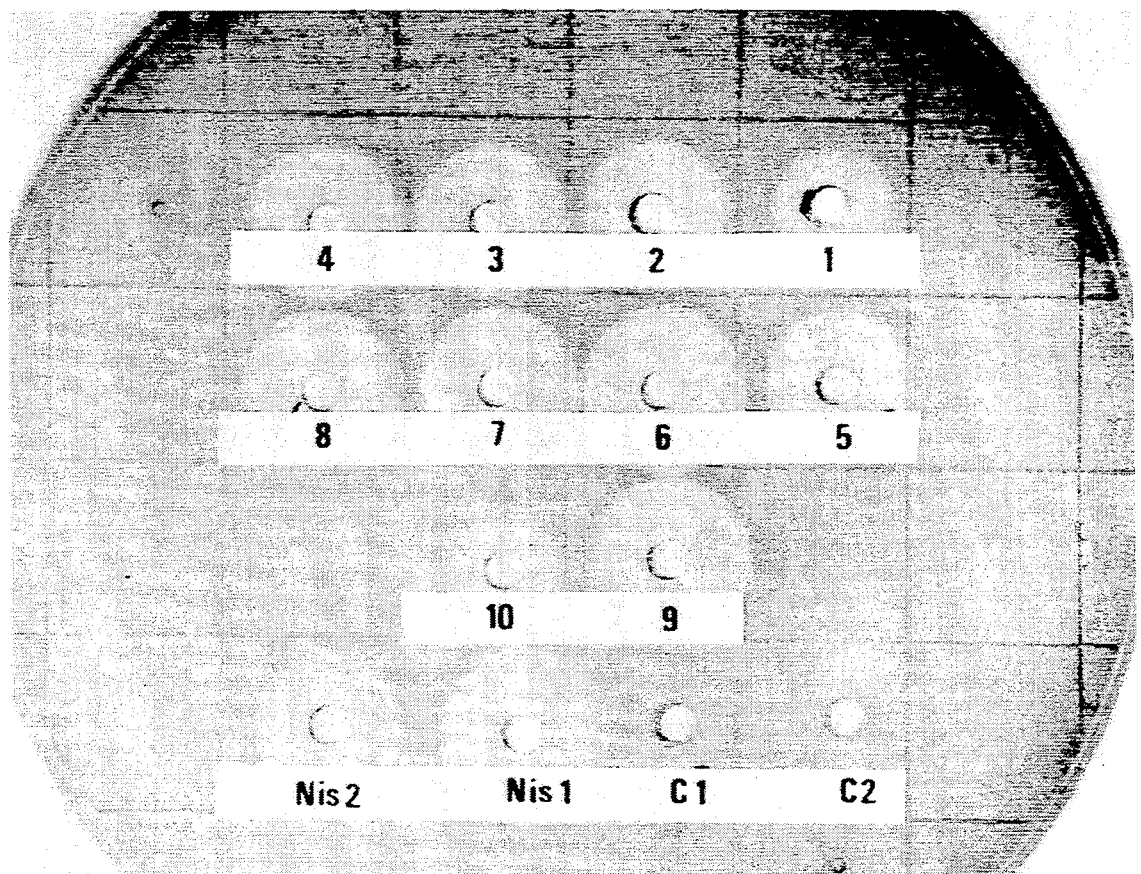
FIG. 3 shows diffusible antimicrobial activity of various concentrations of nisin, adsorbed onto a hydrophilic surface, in the present of a surfactant.

In FIG. 3, the activity of desorbed nisin (from hydrophilic surfaces) is seen as inhibition zones in the agar-well diffusion assay. The amount of recovered nisin roughly corresponded to the relative mass of nisin initially adsorbed to the wafers, similar to the previously described relationships shown in FIGS. 1 and 2. The only exception was the inhibition zone of well 10, wherein the unusually small diameter of the inhibition zone resulted from most of the desorbed nisin being lost during manipulations.

It should be noted that the amount of nisin that became adsorbed onto the wafer surfaces was an amount sufficient for inhibition of susceptible bacteria. Commonly, about 100 Units/g are used in food products to prevent the outgrowth of gram-positive bacterial spores and vegetative cells. The amount of nisin estimated to be adsorbed to the silicon surfaces was between 50 and 100 Units/cm$^2$. This estimate is based on comparisons between inhibition zone diameters of known serial dilutions of nisin versus nisin desorbed from the wafer surfaces (FIG. 3).

While the invention has been described in connection with several embodiments and examples, it will be understood that it is not limited to those embodiments and examples. On the contrary, it is intended to cover all alternatives, modifications, and equivalents as may be included within the spirit and scope of the invention as defined by the appended claims.

We claim:

1. A method for conferring a bacteriocidal characteristic to a substantially solid surface, comprising:
   (a) providing an aqueous solution comprising bacteriocin molecules;
   (b) contacting the solid surface with the solution so as to cause bacteriocin molecules and water molecules to adsorb to the surface;
   (c) removing the surface from contact with the aqueous solution, thereby leaving bacteriocin molecules adsorbed on the surface, the adsorbed bacteriocin molecules retaining a capacity to kill bacteria in and on substances that subsequently contact the surface.

2. A method for conferring a persistent bacteriocidal characteristic to a substantially solid surface, comprising.
   (a) contacting the surface with an aqueous solution comprising molecules of a bacteriocin in a carrier liquid so as to cause a population of molecules consisting essentially of bacteriocin molecules and water molecules to adsorb to the surface;
   (b) removing the surface from contact with the aqueous solution so as to cause bacteriocin molecules to remain adsorbed on the surface, the adsorbed bacteriocin molecules retaining a capacity to kill bacteria in and on substances that subsequently contact the surface.

3. A method as recited in claim 1 further comprising the step, after step (c), of rinsing the surface with water.

4. A method as recited in claim 1 further comprising the step, after step (c), of allowing the surface to dry.

5. A food-packaging material comprising a food-contact surface to which molecules of a bacteriocin are adsorbed such that the food-contact surface exhibits a residual ability to kill bacteria, susceptible to the bacteriocin, in and on substances contacting the surface.

6. A food-preparation surface comprising molecules of a bacteriocin adsorbed to the surface such that the food-preparation surface exhibits a residual ability to kill bacteria, susceptible to the bacteriocin, in and on substances contacting the surface.

7. A package for containing food, comprising a material having a food contact surface to which molecules of a bacteriocin are adsorbed such that the food contact surface exhibits a residual ability to kill bacteria, susceptible to the bacteriocin, in and on substances contacting the surface.

8. An article exhibiting antimicrobial activity comprising a substantially solid surface to which bacteriocin molecules are covalently attached.

9. An article exhibiting antimicrobial activity, comprising a substantially solid surface to which microcapsules containing molecules of a bacteriocin are attached.

* * * * *

UNITED STATES PATENT AND TRADEMARK OFFICE
CERTIFICATE OF CORRECTION

PATENT NO. : 5,451,369
DATED : September 19, 1995
INVENTOR(S) : DAESCHEL ET AL.

It is certified that error appears in the above-indentified patent and that said Letters Patent is hereby corrected as shown below:

On the Cover Page:

Under the heading "[56] References Cited - U.S. PATENT DOCUMENTS" insert the following: --4,597,972 7/1986 Taylor . . . . 423/334 X--.

Column 3, line 57, "Leuconostoc" should be --*Leuconostoc*--.

Column 3, line 63, "Bifidobacterium" should be --*Bifidobacterium*--.

Column 7, line 27, "ohm.cm" should be --ohm·cm--.

Column 7, lines 55-56, after "properties" insert a comma --,--.

Column 12, line 27, delete the period "." and in lieu thereof insert a colon --:--.

Signed and Sealed this

Nineteenth Day of March, 1996

Attest:

BRUCE LEHMAN

Attesting Officer

Commissioner of Patents and Trademarks